(12) United States Patent
Mueller et al.

(10) Patent No.: US 12,265,047 B2
(45) Date of Patent: Apr. 1, 2025

(54) SENSOR, INCLUDING A DIAPHRAGM THAT IS OPEN THROUGH A CLEARANCE, FOR MEASURING THE CONCENTRATION OF AN ANALYSIS FLUID

(71) Applicant: Robert Bosch GmbH, Stuttgart (DE)

(72) Inventors: Renate Mueller, Reutlingen (DE); Helmut Grutzeck, Kusterdingen (DE); Stefan Zehringer, Reutlingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 310 days.

(21) Appl. No.: 17/634,415

(22) PCT Filed: Sep. 21, 2020

(86) PCT No.: PCT/EP2020/076282
§ 371 (c)(1),
(2) Date: Feb. 10, 2022

(87) PCT Pub. No.: WO2021/078449
PCT Pub. Date: Apr. 29, 2021

(65) Prior Publication Data
US 2022/0317078 A1    Oct. 6, 2022

(30) Foreign Application Priority Data
Oct. 21, 2019    (DE) ..................... 10 2019 216 129.4

(51) Int. Cl.
*G01N 27/18*    (2006.01)
*G01N 33/00*    (2006.01)
(52) U.S. Cl.
CPC .......... *G01N 27/18* (2013.01); *G01N 33/0027* (2013.01)
(58) Field of Classification Search
CPC ..................... G01N 27/18; G01N 33/0027
See application file for complete search history.

(56) References Cited

U.S. PATENT DOCUMENTS 4,294,679 A * 10/1981 Maurer .............. G01N 27/4071
   204/426
7,104,112 B2 * 9/2006 Bonne .............. G01N 35/00871
   73/23.24

FOREIGN PATENT DOCUMENTS

CN           1113321      * 12/1995
DE      102017215527 A1    3/2019
(Continued)

OTHER PUBLICATIONS

International Search Report for PCT/EP2020/076282, Issued Dec. 18, 2020.

(Continued)

*Primary Examiner* — Jamel E Williams
*Assistant Examiner* — Alex T Devito
(74) *Attorney, Agent, or Firm* — NORTON ROSE FULBRIGHT US LLP; Gerard A. Messina (57) ABSTRACT

A sensor for measuring a concentration of an analysis fluid based on a thermal conductivity principle. The sensor includes at least one analysis heating element, situated on a measuring diaphragm, for heating the analysis fluid, and a reference heating element, situated on a reference diaphragm, for heating at least one reference gas. The measuring diaphragm and the reference diaphragm are adjacently situated between a sensor substrate and a cap substrate. The measuring diaphragm is situated in a measuring volume and the reference diaphragm is situated in a reference volume. The measuring diaphragm and the reference diaphragm each include at least one coating. The measuring diaphragm is opened by at least one clearance. A method for manufacturing a sensor is also described.

19 Claims, 7 Drawing Sheets

(56) References Cited

FOREIGN PATENT DOCUMENTS

| EP | 2431737 A1 | | 3/2012 |
|----|------------|---|--------|
| EP | 2522972 A2 | | 11/2012 |
| JP | H01155260 | * | 6/1989 |
| JP | 2004037180 | * | 2/2004 |
| JP | 2009168649 A | | 7/2009 |
| JP | 2016017926 A | | 2/2016 |

OTHER PUBLICATIONS

De Graaf G et al., "Micro Thermal Conductivity Detector With Flow Compensation Using a Dual Mems Device," Sensors and Actuators A: Physical, vol. 249, 2016, pp. 186-198.

* cited by examiner

SENSOR, INCLUDING A DIAPHRAGM THAT IS OPEN THROUGH A CLEARANCE, FOR MEASURING THE CONCENTRATION OF AN ANALYSIS FLUID

FIELD

The present invention relates to a sensor for measuring a concentration of an analysis fluid based on a thermal conductivity principle, including at least one analysis heating element, situated on a measuring diaphragm, for heating the analysis fluid, and a reference heating element, situated on a reference diaphragm, for heating at least one reference gas. Moreover, the present invention relates to a method for manufacturing this type of sensor.

BACKGROUND INFORMATION

For gas sensors that operate according to resistive measuring principles, the gas or gas mixture to be measured directly influences the conductivity of a gas-sensitive sensor element. This change in resistance is used as a measured variable for a concentration of the gas or gas mixture. The gas-sensitive sensor element may be a sensor layer or a heating element. For example, one or multiple heating elements in the form of platinum heaters may be situated on a diaphragm. The heating of the heating elements and/or sensor elements is a function of the thermal conductivity of the surrounding gas or gas mixture.

These heating elements may be operated at constant current or at constant power, and at a temperature that is higher than the ambient temperature.

For example, for measuring a hydrogen concentration, use may be made of the better thermal conductivity of hydrogen of 1810 µW/cmK compared to the thermal conductivity of air of 260 µW/cmK.

If hydrogen is present in the surroundings of the heating element, due to the higher thermal conductivity of the hydrogen and an accompanying greater heat dissipation, the temperature of the heating element drops, and its resistance is thus reduced. This change in resistance, i.e., the additional heating power that must be applied to keep the heating element at constant temperature, is proportional to the concentration of the hydrogen. Since the thermal conductivity is a function of the ambient temperature, the ambient temperature may be measured with the aid of a further temperature sensor, for example.

However, the use of such sensors at elevated pressures of the analysis gas, such as greater than 500 mbar positive pressure, is problematic due to the fact that the measuring diaphragm may deform and rupture.

SUMMARY

An object of the present invention includes providing a sensor that is reliably operable under high humidity and high pressure.

This object may be achieved via the present invention. Advantageous embodiments of the present invention are disclosed herein.

According to one aspect of the present invention, a sensor for measuring a concentration of an analysis fluid based on a thermal conductivity principle is provided. The sensor includes at least one analysis heating element, situated on a measuring diaphragm, for heating the analysis fluid, and a reference heating element, situated on a reference diaphragm, for heating at least one reference gas.

In accordance with an example embodiment of the present invention, the measuring diaphragm and the reference diaphragm are adjacently situated between a sensor substrate and a cap substrate, the measuring diaphragm being situated in a measuring volume, and the reference diaphragm being situated in a reference volume.

The measuring diaphragm and the reference diaphragm each include at least one coating, the measuring diaphragm being open through at least one clearance. The coating may preferably cover the diaphragm, at least in areas, and may thus protect the diaphragm. In particular, the coating may cover electrical lines, such as those on the heating elements and/or measuring elements situated on the diaphragms, and may thus protect the electrically conductive coating material from corrosion, oxidation, and aging processes.

The sensor may be made up, for example, of three wafer-shaped layers that are stacked one on top of the other and joined by glass frit, or alternatively via an anodic bond or optionally by adhesion. The wafer-shaped layers may include a cap substrate, a sensor substrate, and a base substrate. In addition, the sensor may also include further layers, the cap substrate or the wafer-shaped cap layer being optional. A reference cavity or a reference volume and a measuring cavity or a measuring volume are formed in the sensor. During manufacture of the sensor, a plurality of such sensor sections may be manufactured and divided into a plurality of sensors via a separation step.

The measuring diaphragm is preferably situated in the measuring volume, and the reference diaphragm is preferably situated in the reference volume. Heating elements are integrated into each diaphragm for carrying out concentration measurements.

The measuring volume and the reference volume are preferably separate from one another so that an exchange of fluids or moisture is prevented. The sensor may thus at the same time function as a barrier against undesirable media. Such an undesirable medium may be, for example, moist air from exhaust gases of a fuel cell vehicle.

For example, if a heat flow of an analysis heating element through a supplied analysis fluid changes, a difference signal may be ascertained between the analysis heating element and the reference heating element. The analysis fluid may be present in a gaseous or liquid form. Due to the coating, the analysis heating element and the reference heating element may be protected from direct contact with the analysis fluid, thus making it possible to prolong the service life of the sensor.

Since the measuring diaphragm includes at least one clearance, it has an open design. Due to this measure, the sensitivity to measured variables or the insensitivity to interfering influences may be increased. In particular, as a result of the clearance, the problem of the deformation of the measuring diaphragm under externally applied pressures that differ from ambient pressure may be eliminated. Such ambient pressures may be, for example, 500 mbar in a muffler of an exhaust gas pipe. In addition, due to the open design of the measuring diaphragm, new fields of application having elevated pressures greater than 2 bar may be provided for the sensor. As a result, the sensor may also be used in a fuel cell vehicle, for example in an anode path under fairly high pressure. Furthermore, the sensor may be used, for example, to test moist exhaust gas or H2 in the exhaust gas of a fuel cell vehicle or in the immediate vicinity of the anode and cathode in the cell stack. The use of an open, coated measuring diaphragm thus enables high pressure stability and the testing of moist or corrosive fluids.

An open diaphragm is understood to mean that at least one hole, a clearance or the like, is situated in the diaphragm, so that a fluid exchange between both diaphragm surfaces is possible. Similarly, with an open volume a fluid exchange may take place with the surroundings or with an arbitrary reservoir.

By the use of a thin, for example nitridic, protective layer on the front side and/or rear side of the measuring diaphragm, damage to the diaphragm due to high moisture levels, or a change in or aging of the embedded heating element/heating resistor due to intercalation of moisture in overlying layers, may be prevented. In subsequent manufacturing processes, the coating may either be removed for a glass frit bond or provided with a thin oxide layer. The analysis heating element and the reference heating element for the concentration measurement may be designed as combined heating/sensor elements. Alternatively, analysis measuring elements may be provided in addition to analysis heating elements, and reference measuring elements may be provided in addition to the reference heating elements.

In accordance with an example embodiment of the present invention, the opening or clearance of the measuring diaphragm and/or of the reference diaphragm may be created via one or multiple holes, for example with the aid of wet etching processes or plasma etching processes. An increase in the sensitivity to the analysis fluid may be reduced by a two-sided flow of the analysis fluid around the measuring diaphragm. In addition, the clearance in the measuring diaphragm is used to decouple the measuring diaphragm from the ambient pressure. Depending on the design of the sensor, the cap substrate may close off the measuring volume in order to separate the measuring volume from the reference volume.

According to one exemplary embodiment of the present invention, the at least one analysis heating element and the at least one reference heating element are connectable to a sensor-external or sensor-internal evaluation electronics system for measuring a change in resistance of the analysis heating element relative to an electrical resistance of the reference heating element, caused by the analysis fluid. Due to this measure, the number of electrically conductive tracks and heating elements on the sensor may be minimized. In particular, strip conductor crossings on the sensor may be avoided or minimized. The necessary strip conductor crossings may be carried out in the evaluation circuit or the evaluation electronics system, which generally contains the levels necessary for this purpose.

The evaluation electronics system may be designed as a complex circuit technology, such as an ASIC or a µcontroller. It is thus possible to provide the strip conductors symmetrically on the measuring chip or the sensor, thus reducing manufacturing tolerances. In addition, sensor exposure masks and process steps on the sensor may be dispensed with due to a reduced number of strip conductors on the sensor.

According to a further specific embodiment of the present invention, the coating is designed as a one-sided or two-sided coating. The coating may thus encompass the entire measuring diaphragm. In particular, the coating may also enclose the at least one clearance introduced into the measuring diaphragm, so that the measuring diaphragm is completely protected. Damage to the measuring diaphragm due to high moisture levels, or a change in or aging of the embedded heating element or heating resistor due to intercalation of moisture in overlying layers, may thus be prevented.

According to a further exemplary embodiment of the present invention, the reference volume is open at the front side and/or at the rear side, or the reference volume is designed as a closed volume. The reference diaphragm is preferably formed as a closed diaphragm or as an open diaphragm, i.e., provided with one or multiple clearances. The reference diaphragm may be adapted to different fields of application as a result of this measure.

According to a further specific embodiment of the present invention, the measuring volume includes at least one fluid channel that is connected at the front side, the rear side, and/or the lateral side, the fluid channel being introduced into a cap substrate, a base substrate, and/or the sensor substrate. The analysis fluid may thus be led through the fluid channel in the measuring volume in different ways. In particular, the fluid channel may be formed in such a way that a particularly rapid or cost-efficient manufacture of the sensor is made possible.

According to a further exemplary embodiment of the present invention, the coating includes at least one nitride, silicon, oxide, plastic, and/or ceramic. The measuring diaphragm may be designed as an oxide-nitride-oxide diaphragm, for example, or alternatively or additionally may be designed as an oxide diaphragm. The listed materials may be used individually or in combination. In addition, thin silicon layers and oxidic, nitridic, or mixed layers are usable as coatings. Thin plastic films, plastic coatings, or ceramic materials are also possible as further alternative or additional materials for the coating.

According to a further specific embodiment of the present invention, the measuring volume and the measuring diaphragm and/or the reference volume and the reference diaphragm have a rectangular, square, or circular cross section. As a result of this measure, the measuring volume and the reference volume may be formed using different manufacturing processes. In particular, the shape of the reference volume and of the measuring volume may be adapted to an external dimension of the sensor. The measuring diaphragm may have a shape that corresponds to the cross section of the measuring volume. The reference diaphragm may likewise have a shape that corresponds to the cross section of the reference volume.

According to a further exemplary embodiment of the present invention, the measuring volume and the reference volume have the same size or have different sizes. If the reference volume is filled with different gases or pressures than the measuring volume, for high accuracy it is advantageous to compensate for the thermal conductivity. For example, the reference volume and the measuring volume may be dimensioned relative to one another in such a way that the measuring volume for 0% H2 content has the same thermal conductivity as the reference volume. A difference bridge voltage, i.e., the measuring signal, is thus essentially 0 V or is some other fixed offset, as the result of which the evaluation electronics system does not detect a signal until there is significant H2 content. The dimension of the measuring volume and of the reference volume may be adjusted via the height of the particular volume and/or via different cavity sizes.

According to a further specific embodiment of the present invention, the sensor includes at least two analysis heating elements and at least two reference heating elements, the analysis heating elements and reference heating elements being usable as heating elements and/or measuring elements for a change in resistance. At least two resistors may preferably be situated in each case on the reference diaphragm and the measuring diaphragm. These resistors are connected to one another in the form of a Wheatstone bridge circuit. Two reference heating elements and two analysis heating elements may simultaneously function as measuring shunts. For the bridge circuit, a first and a fourth measuring shunt may be situated on the measuring diaphragm, and a second and a third measuring shunt may be situated on the reference diaphragm. A particularly sensitive measurement of changes in the resistance values is possible in the area of the medium voltage taps between the first and the third measuring shunts or between the second and the fourth measuring shunts. The measuring signal may be provided at these positions. The measuring shunts may be used as heating elements and also as measuring elements. A design in which the heating elements and the measuring elements are separate is likewise possible.

According to a further exemplary embodiment of the present invention, the closed reference diaphragm separates a first reference volume, introduced into the cap substrate, from a second reference volume introduced into the sensor substrate, the first reference volume and the second reference volume being filled with the same fluid or with different fluids. By use of this measure, different fluids that are not miscible with one another may, in the form of multiple reference volumes, be connected to the reference diaphragm. For example, a reduction of the variable field, for example due to an H2 gas in a cap-side volume and an O2 gas in a sensor substrate-side or base-side volume, may thus be achieved. The reference volume may also be divided into more than two volumes.

According to a further aspect of the present invention, a method for manufacturing a sensor is provided. A wafer-shaped sensor layer is provided in one step. A diaphragm layer is subsequently deposited onto the sensor layer. Further intermediate layers for increasing the connection quality and/or for reducing heat transfer between the diaphragm layer and the sensor layer are possible, as well as the provision of a mechanically stable support structure for the heating elements.

In accordance with an example embodiment of the present invention, clearances are introduced into the diaphragm layer by material removal in a further step. In addition, analysis heating elements and reference heating elements are applied to the diaphragm layer in the form of metal coatings and structured via a suitable method. At least one coating for protecting the analysis heating elements and reference heating elements and the diaphragm layer is subsequently applied. For a coating that is applied on both sides, a base-side coating may be deposited in an intermediate step prior to applying the diaphragm layer.

A cap layer that is closed or provided with openings is subsequently situated on the diaphragm layer or on the coating of the diaphragm layer. The diaphragm layer is exposed by material removal of the sensor layer to form reference volumes and measuring volumes. This step may preferably be carried out on the rear side or base side.

A base layer that is closed, or open at least in areas, is situated on the sensor layer at the rear side in a further step. The base layer may be open or exposed in areas after the step of connecting to the sensor layer. A wafer arrangement with a plurality of interconnected sensors is formed by this step. A plurality of individual sensors may be produced using a separation operation.

Preferred exemplary embodiments of the present invention are explained in greater detail below with reference to greatly simplified schematic illustrations.

DETAILED DESCRIPTION OF EXAMPLE EMBODIMENTS

Figure 1:
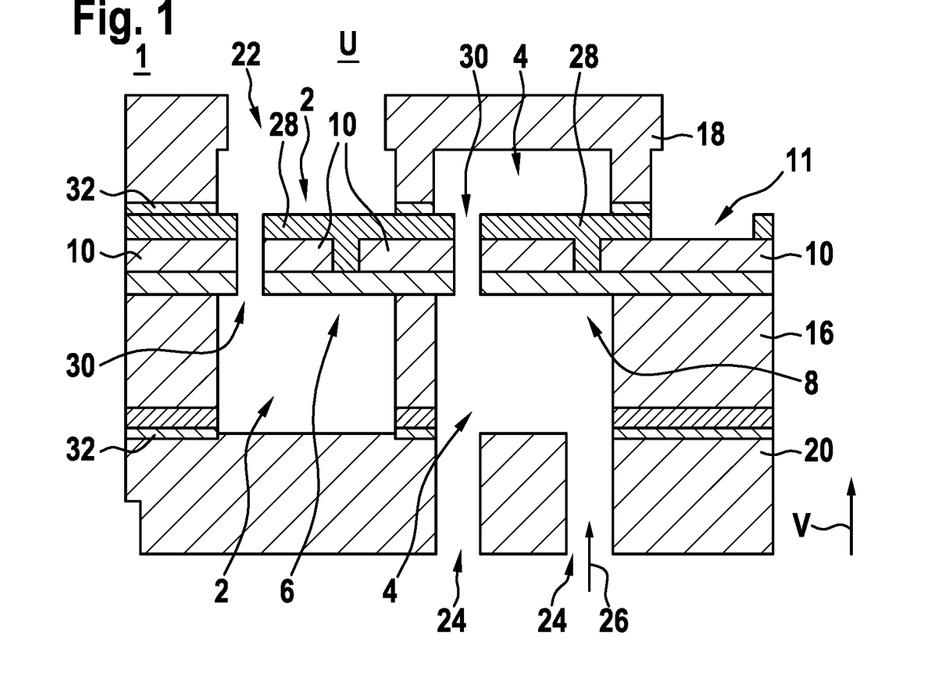
FIG. 1 shows a schematic sectional illustration of a sensor according to a first specific embodiment of the present invention, with an open reference volume.

FIG. 1 shows a schematic sectional illustration of a sensor 1 according to a first specific embodiment, with an open reference volume 2. Sensor 1 includes a measuring volume 4 in addition to reference volume 2. A reference diaphragm 6 is situated in reference volume 2. Measuring volume 4 includes a measuring diaphragm 8. In particular, reference volume 2 and measuring volume 4 are divided in areas by reference diaphragm 6 and measuring diaphragm 8, respectively, and also by cap substrate 18 and base substrate 20.

Figure 12:
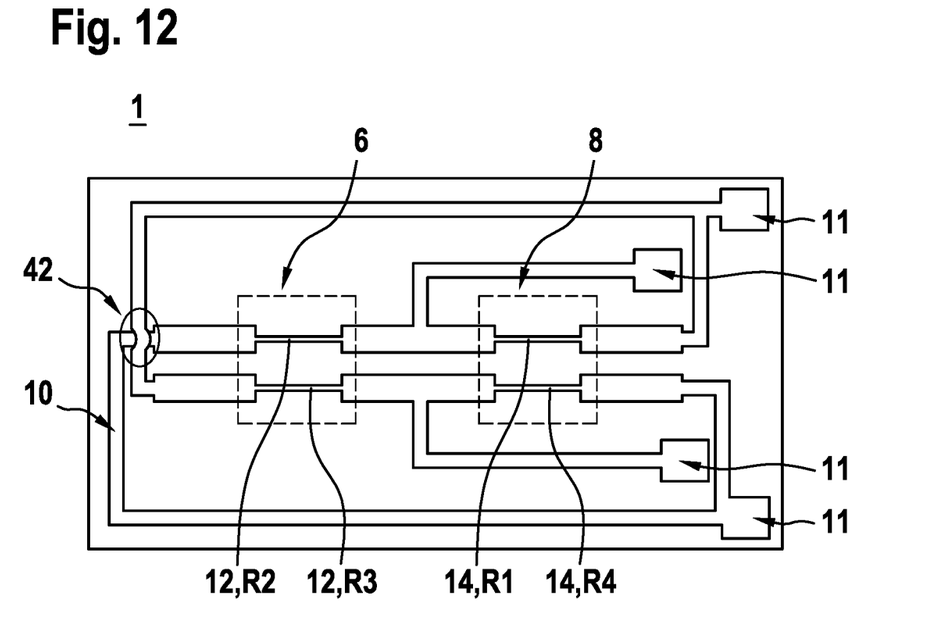
FIG. 12 shows a top view onto the electrical strip conductors of the sensor according to a first exemplary embodiment of the present invention.
Figure 13:
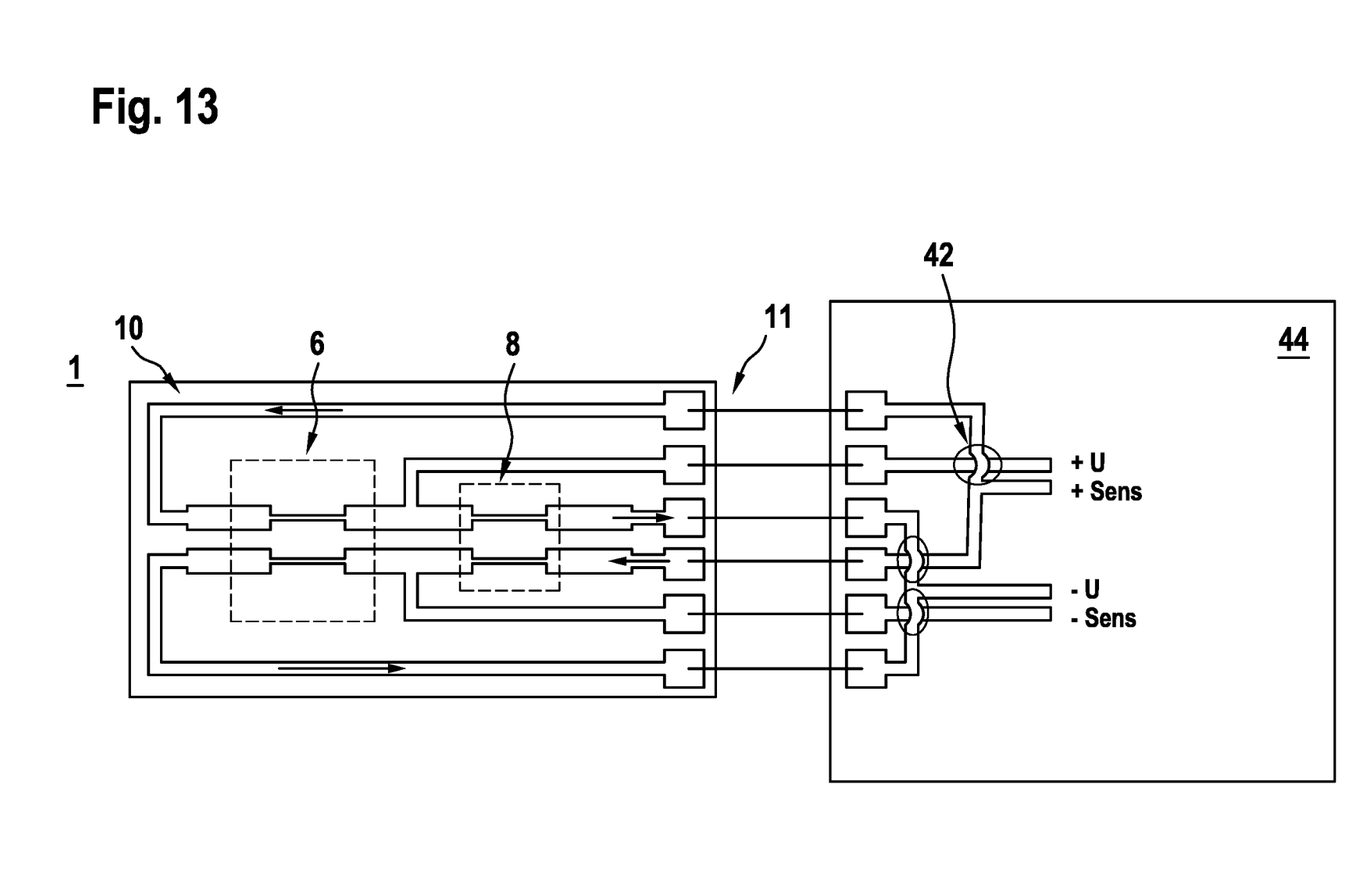
FIG. 13 shows a top view onto the electrical strip conductors of the sensor according to a second exemplary embodiment of the present invention, with a connected evaluation electronics system.

Electrically conductive structures 10 that may be electrically contacted via electrical connections 11 or bond pads are introduced on reference diaphragm 6 and measuring diaphragm 8. Electrically conductive structures 10, illustrated in FIGS. 12 and 13, are designed here as reference heating elements 12 for heating at least one reference fluid, and as analysis heating elements 14 for heating an analysis fluid. Reference heating elements 12 and analysis heating elements 14 are simultaneously used for heating and for measuring changes in resistance or differences in resistance.

Reference volume 2 and measuring volume 4 are introduced in the form of cavities into a sensor substrate 16, and extend up to a cap substrate 18. A base substrate 20 is situated at sensor substrate 16 on a side opposite from cap substrate 18. In vertical direction V, cap substrate 18 is spaced apart from sensor substrate 16 via diaphragms 6, 8.

Substrates 16, 18, 20 are flatly extended, and enclose reference volume 2 and measuring volume 4 at least in areas. Reference volume 2 is closed on the base side by base substrate 20. Measuring volume 4 is closed on the cap side by cap substrate 18.

Fluid channels 24 used for supplying an analysis fluid into measuring volume 4 are introduced into base substrate 20. Arrow 26 illustrates the inflow of the analysis fluid.

Measuring diaphragm 8 and reference diaphragm 6 include a coating 28 that covers electrically conducting structures 10 on the cap side and thus protects them. Coating 28 may be made of a nitride, for example. In addition, each diaphragm 6, 8 includes at least one clearance 30 through which a fluid may pass through diaphragm 6, 8 without mechanical stress.

In the illustrated exemplary embodiment, measuring volume 4 is closed in the area of cap substrate 18. Reference volume 2 is provided with an opening 22 via which reference volume 2 may carry out a gas exchange with surroundings U.

Due to measuring volume 4 which is closed on the cap side, an analysis gas such as H2 may flow through fluid channels 24 into measuring volume 4, and may remain there at least temporarily. The analysis gas may also contain water vapor or moist air. Alternatively, the analysis fluid may be present in liquid form or may be made of a liquid. The concentration of any other heat-conducting gas, such as O2, CO2, He, moist air, and the like, may also be measured. Reference volume 2 is open with respect to a housing or an electronics system, not illustrated, and exposed to environmental influences.

Figure 2:
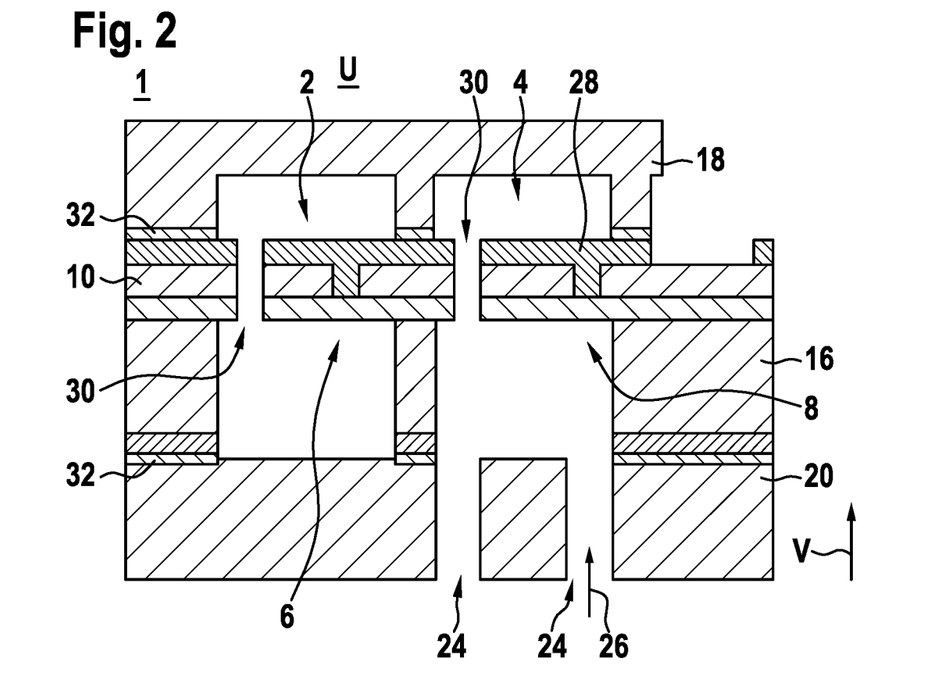
FIG. 2 shows a schematic sectional illustration of a sensor according to a second specific embodiment of the present invention, with a closed reference volume.

FIG. 2 shows a schematic sectional illustration of a sensor 1 according to a second specific embodiment, with a closed reference volume 2. In contrast to the first exemplary embodiment, reference volume 2 is filled with a reference gas that experiences no exchange with surroundings U.

Due to a closed reference volume 2, fluctuations in the ambient air such as changes in moisture or influences from interfering gases from the surroundings may be avoided. Reference volume 2 may be flooded beforehand with a suitable reference fluid, for example during attachment of base substrate 20 or cap substrate 18, for example for bonding with glass frit 32. A reference fluid may be, for example, synthetic air, N2, O2, CO2, methane, and the like.

In addition to expansion of the field of application of sensor 1 for areas with high pressures and/or pressure fluctuations, further advantages are simplified handling during manufacture. For typical semiconductor processes, deposits or residues made up, for example, of ash from lacquer stripping, cleaning solutions, or sludge from sawing the wafer assemblies, may form on diaphragms 6, 8. A closed cap substrate 18 may prevent such deposits.

Figure 3:
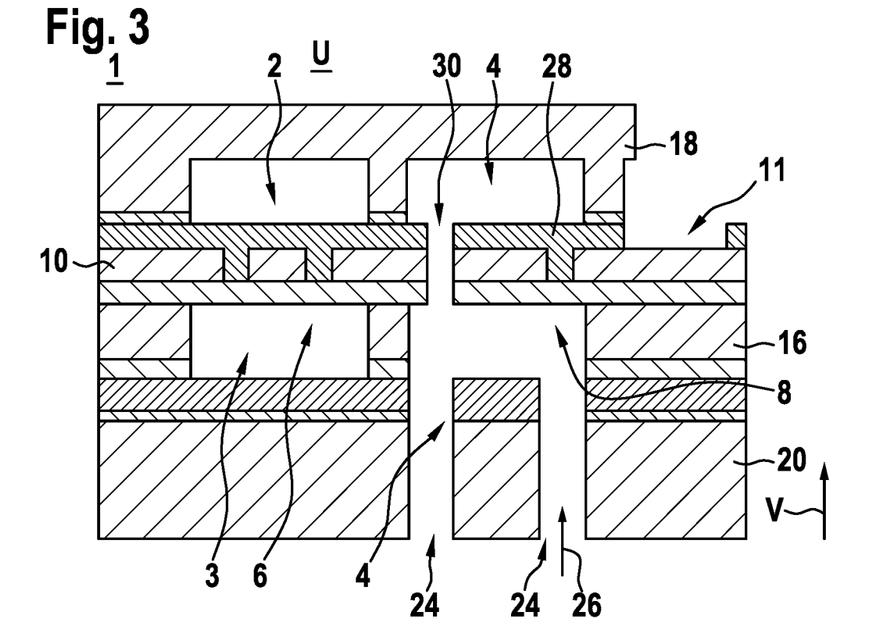
FIG. 3 shows a schematic sectional illustration of a sensor according to a third specific embodiment of the present invention, with two reference volumes that are separate from one another.

FIG. 3 shows a schematic sectional illustration of a sensor 1 according to a third specific embodiment, with two reference volumes 2, 3 that are separate from one another. For this purpose, reference diaphragm 6 has a closed design, i.e., without a clearance 30, as the result of which different fluids are introducible above and below reference diaphragm 6 in vertical direction V.

For example, different gases that are not miscible with one another and that allow a reduction of a variable field may be introduced into reference volumes 2, 3. For example, H2 gas may be led into a first reference volume 2 on the cap side, and O2 gas may be led into a second reference volume 3 on the base side. Creation of further gas-filled reference cavities is also possible.

Figure 4:
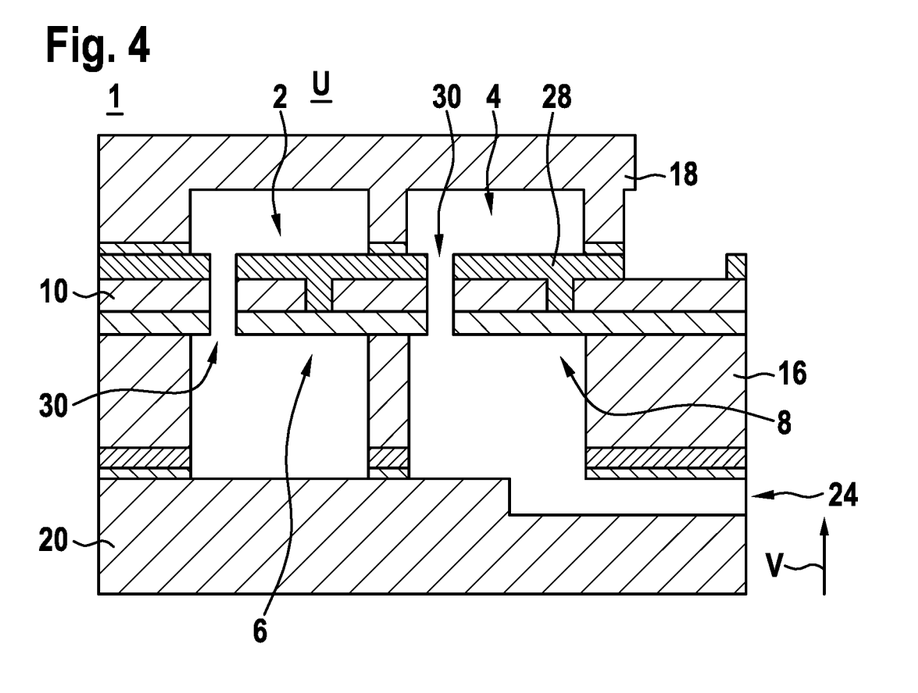
FIG. 4 shows a schematic sectional illustration of a sensor according to a fourth specific embodiment of the present invention, with a laterally extending fluid channel.

FIG. 4 shows a schematic sectional illustration of a sensor 1 according to a fourth specific embodiment, with a laterally extending fluid channel 24. The fluid channel extends not through base substrate 20 in vertical direction V, but, rather, laterally or transversely with respect to vertical direction V along a boundary between base substrate 20 and sensor substrate 16, up to measuring volume 4.

Figure 5:
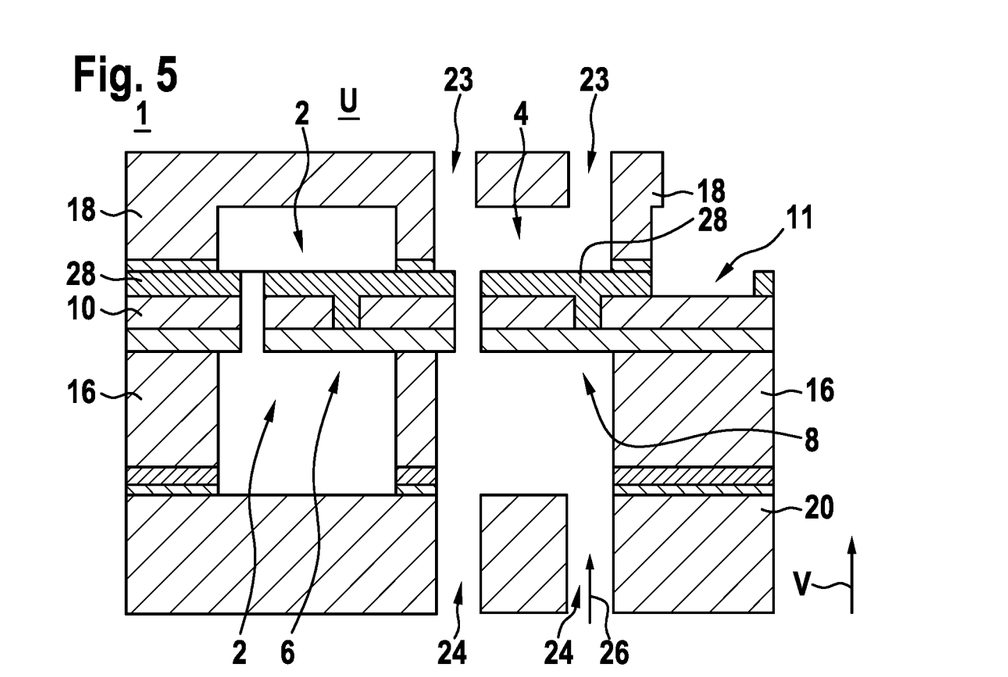
FIG. 5 shows a schematic sectional illustration of a sensor according to a fifth specific embodiment of the present invention, with a measuring volume that is open on two sides.

FIG. 5 shows a schematic sectional illustration of a sensor 1 according to a fifth specific embodiment, with a measuring volume 4 that is open on two sides. It is possible to supply an analysis fluid on the cap side and on the base side. Fluid channels 23 are provided which extend through cap substrate 18 and up to measuring volume 4. Fluid channels 24 are likewise situated in substrate 20 on the base side, through which the analysis fluid may pass into measuring volume 4. The analysis fluid may continuously flow through measuring volume 4 due to such an arrangement.

FIGS. 6 through 11 illustrate a schematic sequence for explaining a method for manufacturing sensor 1. FIGS. 6 through 11 show details of a wafer-shaped arrangement, which is separated to form multiple sensors 1 in a last step. The separation step is not described or illustrated in greater detail.

Figure 6:
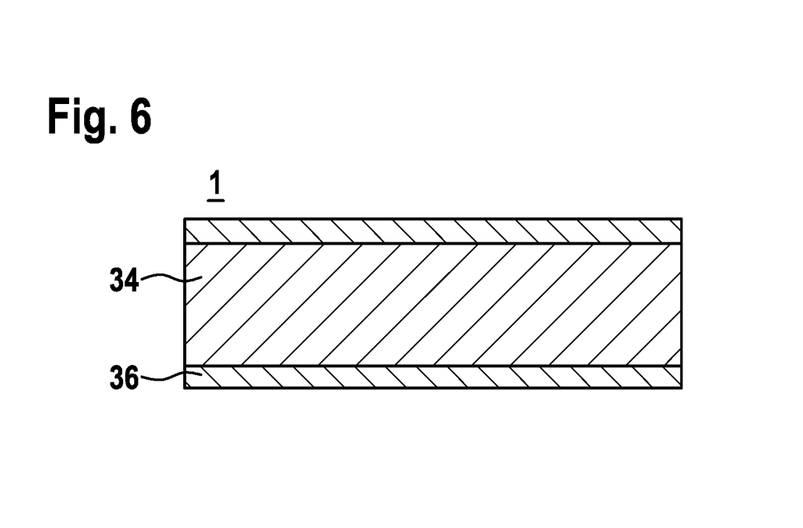
FIGS. 6 through 11 show a schematic sequence for illustrating a method for manufacturing the sensor, in accordance with an example embodiment of the present invention.

FIG. 6 illustrates a step in which a wafer-shaped sensor layer 34 is provided. Sensor layer 34 may be coated with a dielectric 36, for example. The dielectric may be designed as a first diaphragm layer.

Figure 7:
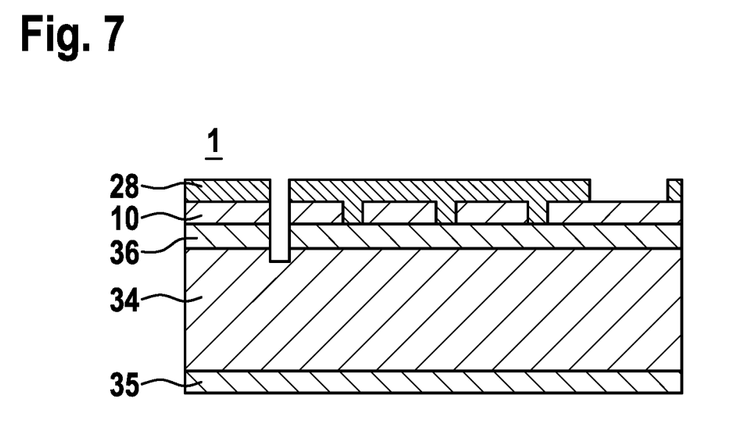

Electrically conductive structures 10 are applied to dielectric 36 in a further step shown in FIG. 7. This step may take place, for example, by sputtering of platinum or some other metal. Structuring via a lithographic method in combination with an etching process may be subsequently carried out.

Analysis heating elements 14 and reference heating elements 12 in the form of metal coatings may be applied to diaphragm layer 36 via the application of electrically conductive structures 10.

Clearances 30 may be subsequently introduced into electrically conductive structures 10 and diaphragm layer 36. Deposition of a coating 28 that is used as protection for electrically conductive structures 10 takes place in a further step. Alternatively or additionally, clearances 30 in electrically conductive structures 10 may also be provided after application of coating 28, or may be provided through coating 28.

For example, coating 28 may be made of an oxide or a nitride, or both. Pressure compensation openings or clearances 30 may be formed in a further step. Clearances 30 may be introduced into diaphragm layer 36, coating 28, and electrically conductive structures 10, for example using a gas-phase etching process or a plasma etching process.

Figure 8:
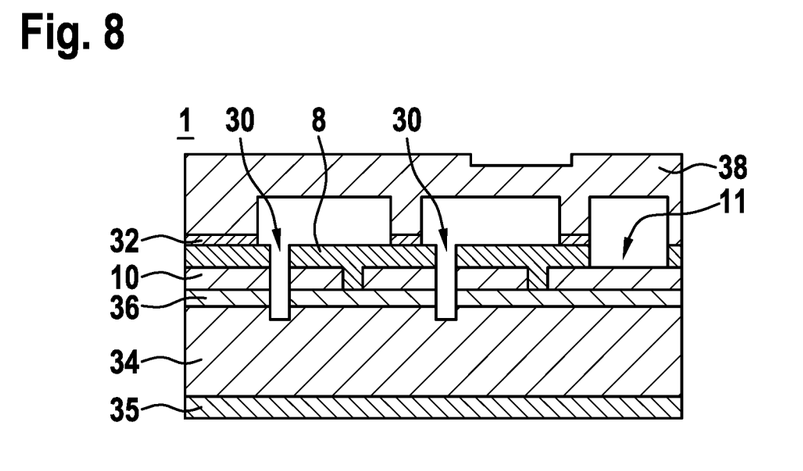

FIG. 8 shows a further step in which a cap layer 38 that is closed or provided with openings 22, 23 is situated on coating 28 of diaphragm layer 36. The adhesion between cap layer 38 and coating 28 may be enabled by applying glass frit 32. Cap layer 38 may already include cavities, which are necessary for forming electrical connections 11, reference volume 2, and measuring volume 4.

In addition, an adhesion promoter layer 35 is also applied to sensor substrate 34 in order to improve the joining process of base substrate 34. This adhesion promoter layer 35 may be made, for example, of an oxide and/or a combination of oxide, nitride, or metal oxides. Depending on the design of sensor 1, this adhesion promoter layer 35 may likewise be structured.

Figure 9:
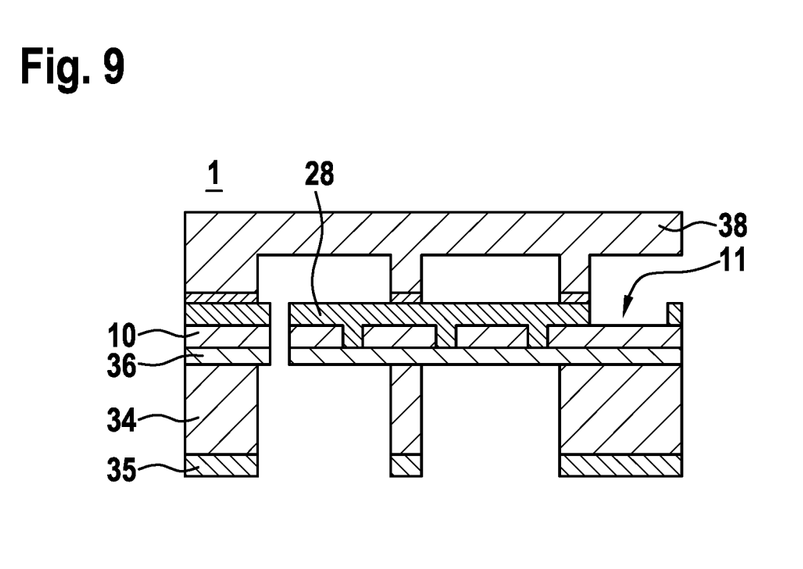

FIG. 9 shows a further step for manufacturing sensor 1. Diaphragm layer 36 is exposed to form reference volume 2 and measuring volume 4 by material removal of the sensor layer. The material removal may take place in one or multiple steps. For example, the material removal may take place by grinding or full-surface thinning and/or via an etching process. The base-side exposure of diaphragm layer 36 may take place using a trench etching process, for example.

Figure 10:
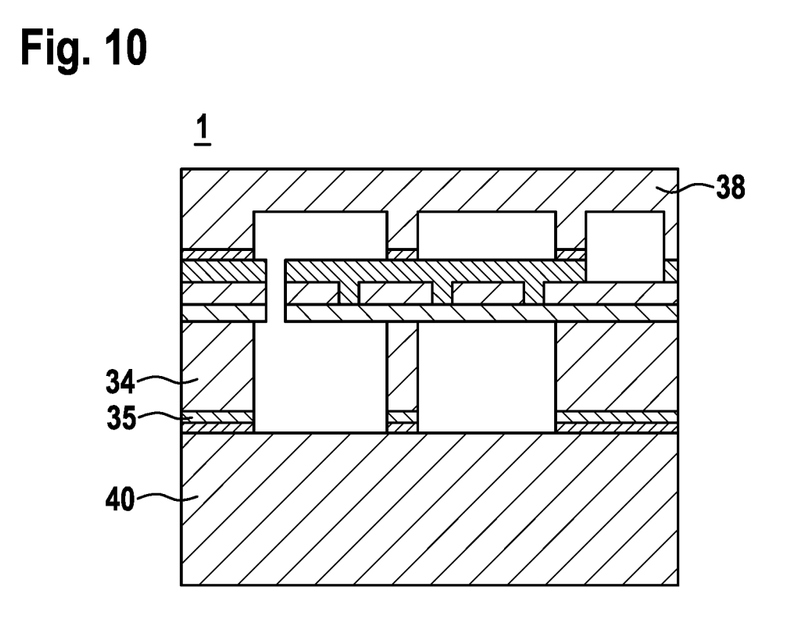
Figure 11:
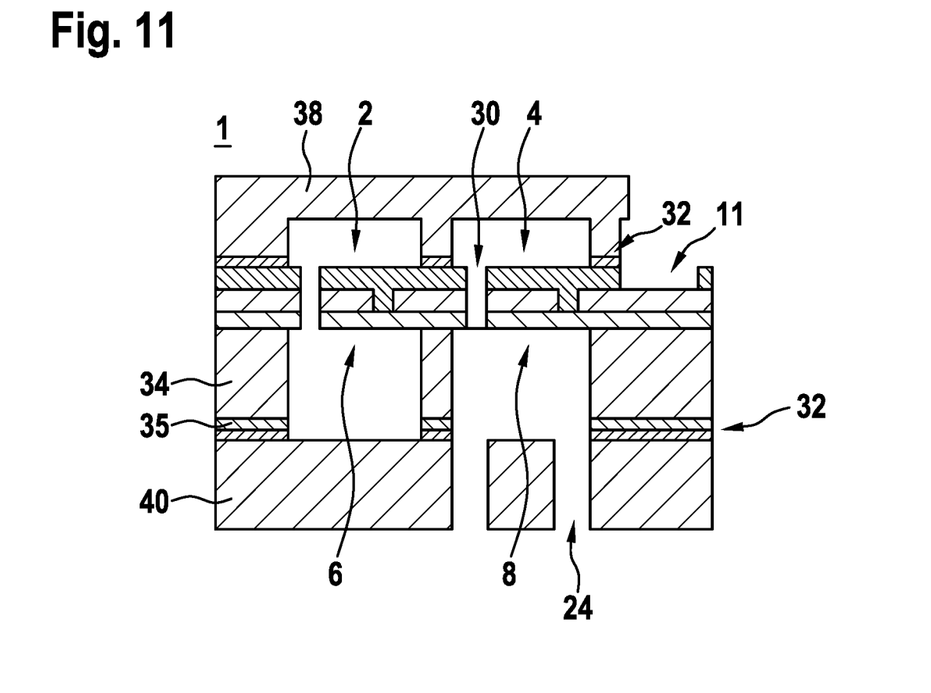

A base layer 40 that is closed, or open at least in areas, is subsequently situated on sensor layer 34. This step is illustrated in FIG. 10. The introduction of fluid channels 24 into base layer 40 is shown in FIG. 11, cap layer 38 and base layer 40 being ground to the final dimensions.

A plurality of sensors 1 is formed using a separation operation.

Alternatively or additionally, for introducing fluid channels 24 into base layer 40, openings 22, 23 may also be formed in cap layer 38. Furthermore, introducing openings 22, 23 in cap layer 38 through clearances 30 is possible.

By use of the method, depths of all cavities or of volumes 2, 4 are controllable in the micron range. The heat transfer may thus be controlled by a targeted flat or particularly deep cavity in cap substrate 18 or sensor substrate 16, and by the shape of volumes 2, 4. For example, the shape of volumes 2, 4 may have a symmetrical or asymmetrical design. For example, depths in the range of 6 µm to 600 µm may be created.

FIG. 12 shows a top view onto electrically conductive structures 10 that are designed as electrical strip conductors of sensor 1. Electrically conductive structures 10 form a cost-efficient form of wiring, since they include only one strip conductor crossing 42 on sensor 1.

Reference heating elements 12 and analysis heating elements 14 are simultaneously used for heating and for measuring changes in resistance or differences in resistance.

Two resistors R1 through R4 that are formed by electrically conductive structures 10 are situated on reference diaphragm 6 and measuring diaphragm 8. These resistors R1 through R4 are connected to one another in the form of a Wheatstone bridge circuit. Resistors R1 and R4 are situated on measuring diaphragm 8, and resistors R2 and R3 are situated on reference diaphragm 6.

A difference of medium voltage taps between resistors R1 and R3 or between R2 and R4 is sensitive to changes in the resistance values, and may therefore be used as a measuring signal.

Resistors R1 through R4 are used both as heating elements and measuring elements. A design in which heating elements and measuring elements are separate is likewise possible.

In the specific embodiment illustrated in FIG. 12, diaphragms 6, 8 or corresponding volumes 2, 4 are the same size and have a square cross section.

FIG. 13 shows a top view onto electrically conductive structures 10 of sensor 1 according to a second exemplary embodiment, with a connected evaluation electronics system 44. In contrast to the exemplary embodiment shown in FIG. 12, in this case no strip conductor crossing 42 is provided on sensor 1. For implementing a Wheatstone bridge circuit, the design of strip conductor crossing 42 is displaced on evaluation electronics system 44. The bond pads or electrical connections 11 may be mounted at some other edge of sensor 1. For example, electrical connections 11 may be rotated by 90° in order to simplify or optimize a subsequent installation of the sensor.

In addition, reference volume 2 has a larger design than measuring volume 4. This is illustrated by reference diaphragm 6, which has a larger design compared to measuring diaphragm 8.

Alternatively, additional measuring resistors or heating resistors may also be provided, for example to measure the ambient temperature or to condition sensor 1 uniformly or at a constant thermal temperature.

What is claimed is:

1. A sensor for measuring a concentration of an analysis fluid based on a thermal conductivity principle, the sensor comprising:

at least one analysis heating element, situated on a measuring diaphragm, configured to heat the analysis fluid;
a reference heating element, situated on a reference diaphragm, configured to heat at least one reference fluid, wherein:
the measuring diaphragm and the reference diaphragm are situated adjacent to each other as parts of a diaphragm layer that is arranged in a plane that is vertically between a sensor substrate and a cap substrate;
the measuring diaphragm is situated in a measuring volume; and
the reference diaphragm is situated in a reference volume;
at least one coating coats each of the measuring diaphragm and the reference diaphragm; and
at least one clearance is situated in the measuring diaphragm via which the analysis fluid is able to flow vertically from one side of the measuring diaphragm facing towards the sensor substrate to an opposite side of the measuring diaphragm facing towards the cap substrate.

2. The sensor as recited in claim 1, wherein the at least one analysis heating element and the at least one reference heating element are connectable to a sensor-external or sensor-internal evaluation electronics system for measuring a change in resistance of the analysis heating element relative to an electrical resistance of the reference heating element, caused by the analysis fluid.

3. The sensor as recited in claim 1, wherein the coating is a one-sided or two-sided coating.

4. The sensor as recited in claim 1, wherein the reference volume is open to an environment surrounding the sensor at a front side and/or at a rear side of the sensor.

5. The sensor as recited in claim 1, wherein the measuring volume includes at least one fluid channel that is connected at a front side, and/or a rear side, and/or a lateral side, the fluid channel being introduced into a cap substrate, and/or a base substrate, and/or the sensor substrate.

6. The sensor as recited in claim 1, wherein the coating includes at least one nitride, and/or silicon, and/or oxide, and/or plastic, and/or ceramic.

7. The sensor as recited in claim 1, wherein the measuring volume and the measuring diaphragm and/or the reference volume and the reference diaphragm, have a rectangular, or square, or oval, or circular cross section.

8. The sensor as recited in claim 1, wherein the measuring volume and the reference volume have the same size or have different sizes.

9. The sensor as recited in claim 1, wherein the sensor includes at least two analysis heating elements and at least two reference heating elements, the analysis heating elements and the reference heating elements being usable as heating elements and/or measuring elements for a change in resistance.

10. The sensor as recited in claim 1, wherein the reference volume is open to an environment surrounding the sensor via an opening in the cap substrate.

11. The sensor as recited in claim 10, wherein the measuring volume is closed to the environment at a side of the measuring diaphragm facing towards the cap substrate and is open for introduction of the analysis fluid into the measuring volume via an opening in the sensor substrate.

12. The sensor as recited in claim 1, wherein the reference volume is a closed volume between the cap substrate and the sensor substrate, with fluid being unable to enter into the reference volume through the cap substrate and being unable to enter into the reference volume through the sensor substrate.

13. The sensor as recited in claim 12, wherein the measuring volume is closed to the environment at a side of the measuring diaphragm facing towards the cap substrate and is open for introduction of the analysis fluid into the measuring volume via an opening in the sensor substrate.

14. The sensor as recited in claim 1, wherein the reference volume is open at a front side and/or at a rear side, or the reference volume is a closed volume, the reference diaphragm being formed as a closed diaphragm or as a diaphragm that is provided with a clearance.

15. The sensor as recited in claim 1, wherein the reference diaphragm is a closed diaphragm without any clearance via which fluid can flow vertically from one side of the reference diaphragm facing towards the sensor substrate to an opposite side of the reference diaphragm facing towards the cap substrate.

16. The sensor as recited in claim 1, wherein the reference diaphragm includes a clearance via which the reference fluid is able to flow vertically from one side of the reference diaphragm facing towards the sensor substrate to an opposite side of the reference diaphragm facing towards the cap substrate.

17. A sensor for measuring a concentration of an analysis fluid based on a thermal conductivity principle, the sensor comprising:

at least one analysis heating element, situated on a measuring diaphragm, configured to heat the analysis fluid;
a reference heating element, situated on a reference diaphragm, configured to heat at least one reference fluid, wherein:
  the measuring diaphragm and the reference diaphragm are adjacently situated in the form of a diaphragm layer between a sensor substrate and a cap substrate;
  the measuring diaphragm is situated in a measuring volume;
  the reference diaphragm is situated in a reference volume;
  each of the measuring diaphragm and the reference diaphragm includes at least one coating;
  at least one clearance is situated in the measuring diaphragm; and
  the reference diaphragm separates a first fluid-filled reference volume, which is in the cap substrate, from a second fluid-filled reference volume, which is in the sensor substrate.

18. The sensor as recited in claim 17, wherein the first and second fluid-filled reference volumes are filled with a same fluid as each other.

19. The sensor as recited in claim 17, wherein the first and second fluid-filled reference volumes are filled with different fluids than each other.

* * * * *